United States Patent
Bevis et al.

(10) Patent No.: US 7,002,677 B2
(45) Date of Patent: Feb. 21, 2006

(54) DARKFIELD INSPECTION SYSTEM HAVING A PROGRAMMABLE LIGHT SELECTION ARRAY

(75) Inventors: Christopher F. Bevis, Los Gatos, CA (US); Paul J. Sullivan, Campbell, CA (US); David W. Shortt, Milpitas, CA (US); George J. Kren, Los Altos Hills, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 25 days.

(21) Appl. No.: 10/714,257

(22) Filed: Nov. 14, 2003

(65) Prior Publication Data

US 2005/0018179 A1 Jan. 27, 2005

Related U.S. Application Data

(60) Provisional application No. 60/489,621, filed on Jul. 23, 2003.

(51) Int. Cl.
*G01N 21/88* (2006.01)

(52) U.S. Cl. ................................................. 356/237.5
(58) Field of Classification Search ... 356/237.2–237.5
See application file for complete search history.

(56) References Cited

U.S. PATENT DOCUMENTS

| | | | | |
|---|---|---|---|---|
| 5,046,847 A | * | 9/1991 | Nakata et al. | 356/237.3 |
| 5,659,390 A | * | 8/1997 | Danko | 356/237.4 |
| 6,201,601 B1 | * | 3/2001 | Vaez-Iravani et al. | 356/237.4 |
| 6,366,352 B1 | * | 4/2002 | Goldberg et al. | 356/237.2 |

OTHER PUBLICATIONS

International Search Report dated Jul. 22, 2005 from corresponding International Application No. PCT/US04/11127.

* cited by examiner

*Primary Examiner*—Richard A. Rosenberger
(74) *Attorney, Agent, or Firm*—Beyer Weaver & Thomas LLP

(57) ABSTRACT

An inspection tool embodiment includes an illumination source for directing a light beam onto a workpiece to generate scattered light that includes the ordinary scattering pattern of the workpiece as well as light scattered from defects of the workpiece. The embodiment includes a programmable light selection array that receives light scattered from the workpiece and selectively directs the light scattered from defects onto a photosensor which detects the defect signal. Processing circuitry receives the defect signal and conducts surface analysis of the workpiece that can include the characterizing of defects of the workpiece. The programmable light selection arrays can include, but are not limited to, reflector arrays and filter arrays. The invention also includes associated surface inspection methods.

42 Claims, 12 Drawing Sheets

FIG. 9(a)   FIG. 9(b)

DARKFIELD INSPECTION SYSTEM HAVING A PROGRAMMABLE LIGHT SELECTION ARRAY

RELATED APPLICATION

This application claims priority to the U.S. Provisional Patent Application Ser. No. 60/489,621, entitled "Darkfield Inspection System Having Programmable Light Selection Array", filed on Jul. 23, 2003. The above-referenced application is hereby incorporated by reference in its entirety for all purposes.

TECHNICAL FIELD

The invention described herein relates generally to surface inspection and testing. In particular, the invention relates to devices and methods for darkfield inspection of unpatterned semiconductor wafer surfaces.

BACKGROUND

For many years, darkfield scanning methodologies have been used to scan patterned surfaces. Darkfield scanning makes use of light scattered or diffracted by the surface to characterize and examine features of the surface. As used herein, scattered light shall refer to both scattered light and diffracted light. FIG. 1 is a cross-section view of an illuminated surface used to illustrate aspects of darkfield scanning. An illumination source 101 projects a light beam I (also referred to herein as the incident beam) onto the surface 102 being examined. A portion of the incident beam I is reflected by the surface as the reflected beam R. If the surface 102 was perfectly reflective, the entire incident beam I would be reflected. However, most surfaces have a variety of characteristics which cause a portion of the light from an incident beam I to be scattered. Darkfield scanning makes use of this scattered light.

One particular surface feature that causes light scattering is referred to as a defect. The detection, quantification, and classification of defects is important in many areas. In particular, defect detection and analysis are important in semiconductor processing. Defects include, but are not limited to, pits, bumps, scratches, and a number of other features, which mar the surface 102. Thus, the light of an incident beam I is often subject to some degree of scattering. FIG. 1 illustrates a typical incident beam I having a light scattering pattern schematically depicted by a plurality of scattered light rays 103, 104, 105, and 106, which are scattered by a surface defect 108. The depicted plurality of rays can represent a continuous angular distribution of light scattered and diffracted by the surface.

Most conventional darkfield inspection tools make use of a single discrete photosensor element (for example a photomultiplier tube (PMT)) to detect the light scattered from the inspection surface. Some designs use as many as three or four distinct and widely separated discrete photodetector elements. Such discrete photodetector element(s) are positioned so that they are not in the path of the specular (reflected) beam R. This results in a detection field where the background (the field) is dark. The scattered light received by the detector provides a representation of the surface 102 whereby the surface defects show up as lighter regions against the dark background or field. Hence, the name darkfield scanning.

In a typical inspection tool, an illumination source directs an incident light beam onto the surface being inspected (i.e., a workpiece that is commonly, but not exclusively, a semiconductor wafer). If the surface were perfectly reflective, all light would be reflected in the specular direction (R of FIG. 1). However, under most conditions, even the highest quality wafers (or other surfaces) have some degree of surface roughness which causes scattering of the incident light beam. Moreover, surface imperfections and other defects give rise to further scattering. It is this concept of light scattering by surface defects that forms the foundation of conventional darkfield inspection techniques used for defect detection.

FIGS. 2(a) and 2(b) depicts cross-section views of a surface being scanned using darkfield scanning. The surface 102 is illuminated by an incident beam I, a portion of which is reflected as reflected beam R. Other portions of the incident beam I are scattered. FIG. 2(a) depicts the scatter from the surface 102 in the absence of a defect. Since ordinary surfaces are not perfect the incident light is scattered at a number of different angles. This results in a three-dimensional angular light distribution that can be different for each wafer depending on surface characteristics (e.g., surface topography, thickness and type of materials used, the layered structure of the surface, and so on) and other factors. This three-dimensional angular light distribution is referred to herein as the ordinary scattering pattern 200 of the surface 102 being inspected. Because FIG. 2(a) is a two dimensional representation of a three dimensional reality, only one range of scattering angles is depicted for the ordinary scattering pattern 200. In actuality the scattering angles of the ordinary scattering pattern 200 extend into and out of the page.

FIG. 2(b) depicts the same surface 102 as depicted in FIG. 2(a) except that the surface has a defect D formed thereon. The presence of the defect D causes the scattering pattern to vary. The defect D scatters some light as, for example, scattered light rays $S_1$, $S_2$, and $S_3$. Additionally, much of the light still falls within the scattering angles defined by the ordinary scattering pattern 200'. It is the measurement of this scattered light that enables the inspection tool to detect and characterize defects in an inspected surface 102.

As depicted in the simplified schematic depiction of FIG. 3(a), in some implementations of conventional darkfield inspection a wafer 300 is placed in a tool and a spiral inspection pattern 301 is performed. During such an inspection the light scattered from the surface of the wafer 300 is detected. The intensity (I) of the scattered light can be plotted over time (t) as depicted in FIG. 3(b). As is commonly the case, the intensity of the scatter increases when the incident beam illuminates a defect. Such a defect signal 302 is schematically depicted. And because in a spiral inspection pattern (as well as many other inspection patterns) time correlated to the position of the defect, the defect can be located and identified. However, due to the small size of the defect, the increase in scattered light intensity can be very slight (as shown by the slight increase in amplitude for the defect signal 302). Thus, one of the challenges in conventional darkfield inspections of this type is to enhance the signal-to-noise ratio (SNR) for such inspection increasing the reliability and sensitivity of such inspections. Thus, what is needed are improved methods and apparatus for receiving and processing defect signals generated using scattered light in inspection processes.

SUMMARY OF THE INVENTION

In accordance with the principles of the present invention, surface inspection tools and methodologies are disclosed. In general, the embodiments of the invention concern inspection tools that selectively exclude the optical signal generated by the ordinary scattering pattern of the surface being inspected. The optical signal remaining after the ordinary scattering pattern has been excluded generally comprises signal generated by defects the surface being inspected. This remaining signal is selectively detected and analyzed to detect and categorize defects of the surface being inspected. Such embodiments and related method provide a higher signal-to-noise ratio than conventional techniques and provide enhanced defect detection and analysis capabilities.

In one embodiment, an inspection tool includes an illumination source for directing a light beam onto a workpiece to generate scattered light that includes the ordinary scattering pattern of the workpiece as well as light scattered from defects of the workpiece. The embodiment includes a programmable light selection array that receives light scattered from the workpiece and selectively directs the light scattered from defects onto a photosensor that translates the light into an electrical signal. Processing circuitry receives the electrical signal from the photosensor and using it to conduct surface analysis of the workpiece that can include the characterizing of defects of the workpiece. Programmable light selection arrays can include, but are not limited to, reflector arrays and filter arrays.

Another embodiment includes an illumination source that directs a light beam onto a workpiece to generate scattered light from the workpiece. A programmable light selection array is positioned to receive the scattered light and direct the light onto a first photodetector array which translates the light into an associated electrical signal. Circuitry receives the electrical signal and determines which portion of the scattered light comprises the ordinary scattering pattern of the workpiece. Based on this determination, the programmable light selection array selectively directs the light scattered from defects of the workpiece onto a photosensor where it is translated into an associated defect signal. The defect signal is analyzed by processing circuitry to conduct surface analysis of the workpiece.

In another embodiment, a surface inspection apparatus includes an illumination source that directs a light beam onto a workpiece and a programmable light selection array that receives light scattered from the workpiece. The programmable light selection array being capable of directing the light onto to a photodetector element and also capable of selectively directing selected portions of the light onto to a photosensor element. The photodetector element receives light from the programmable light selection array and translates it into an associated electrical signal that is received and analyzed by processing circuitry to determine an ordinary scattering portion and a defect portion of the of the light scattered from the workpiece. Control circuitry controls light selection elements of the programmable light selection array so that the defect portion of the light is selectively directed onto the photosensor element which generates a defect signal associated with the defects. Defect analysis circuitry analyzes the defect signal to characterize defects the workpiece In another embodiment, a method for conducting surface inspections is disclosed. The method involves providing a workpiece for inspection and illuminating the workpiece to produce scattered light that includes light scattered from defects in the workpiece causing defect scatter and light scattered from non-defect portions of the workpiece that generate an ordinary scattering pattern of the workpiece. The scattered light is detected and it is determined which of the scattered light comprises the ordinary scattering pattern of the workpiece. This information can be used to selectively detect the defect scatter which is analyzed to characterize the workpiece surface.

These and other aspects of the present invention are described in greater detail in the detailed description of the drawings set forth hereinbelow.

BRIEF DESCRIPTION OF THE DRAWINGS

The following detailed description will be more readily understood in conjunction with the accompanying drawings, in which:

FIGS. 9(a)–9(c) are simplified schematic views of an un-patterned wafer having an epitaxially grown wafer surface and an ordinary scattering pattern resulting from illumination thereof.

It is to be understood that, in the drawings, like reference numerals designate like structural elements. Also, it is understood that the depictions in the Figures are not necessarily to scale.

DETAILED DESCRIPTION OF THE DRAWINGS

The present invention has been particularly shown and described with respect to certain embodiments and specific features thereof. The embodiments set forth herein below are to be taken as illustrative rather than limiting. It should be readily apparent to those of ordinary skill in the art that various changes and modifications in form and detail may be made without departing from the spirit and scope of the invention.

The following detailed description describes various embodiments of surface inspection tools and methods for their use. In particular, embodiments of the present invention illuminate a portion of an unpatterned surface to create scattered light. The scattered light is selectively detected. Such selective detection is concentrated on detecting scattered light caused by defects of the surface while substantially reducing the amount of light detected from the ordinary scattering pattern. In many embodiments, such selective detection is effectuated through the use of light selection arrays which are described in detail below.

It has been discovered by the inventors that un-patterned wafers have an ordinary scattering pattern that generally results from illumination of most of the non-defect containing portions of the surface. The ordinary scattering pattern can be characterized by an angular light scattering distribution. Additionally, the inventors have discovered that, in general, defect induced scattering scatters at a different angular distribution than the ordinary scattering pattern. Thus, light scattered by defects is scattered at one range of angle and the light of the ordinary scattering pattern is scattered at a different range of angles. Additionally, because defects occupy such a small portion the wafer surface, the vast majority of the scattered light generated by illumination of the surface corresponds to the ordinary scattering pattern. Thus, by scanning an entire wafer (or some portion thereof), a light scattering pattern that generalizes the wafer can be determined. Moreover, because the ordinary scattering pattern generally does not provide much information usable for detecting defects and contributes significantly to noise in a defect detection signal, it is advantageous for an inspector to detect only the light scattered by the defects. Such detection can reduce the SNR and increase the sensitivity of defect detection and characterization.

Figure 1:
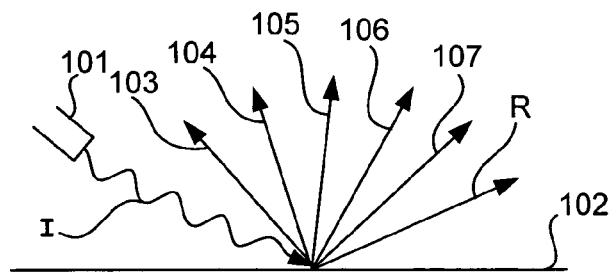
FIG. 1 is a simplified schematic cross-sectional view showing an incident light beam being scattered from a semiconductor wafer surface.
Figure 2A:
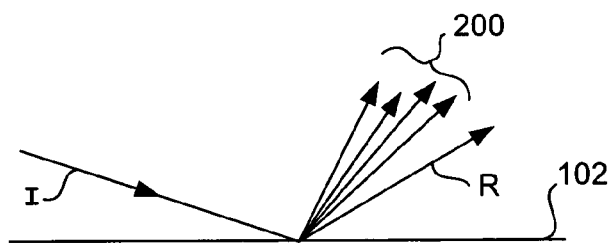
FIGS. 2(a) and 2(b) are simplified schematic cross-sectional views showing an incident light beam being scattered from a semiconductor wafer surface both with and without a defect showing resultant scattering patterns.
Figure 2B:
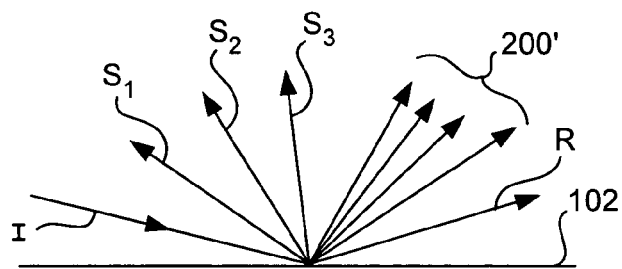
Figure 3A:
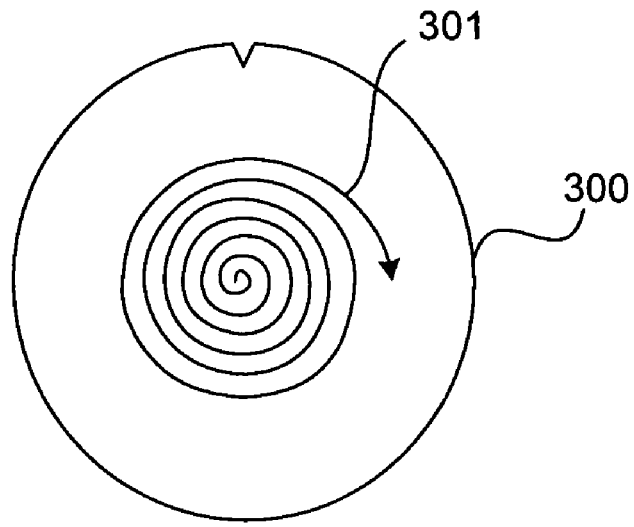
FIG. 3(a) is a schematic top down view of a wafer showing an exemplar spiral inspection pattern.
Figure 3B:
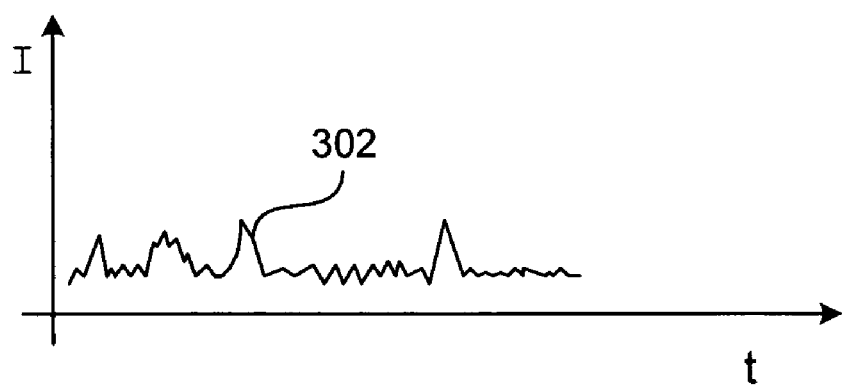
FIG. 3(b) is a graphical depiction of scattered light intensity over time resulting from the inspection process depicted in FIG. 3(a).
Figure 4A:
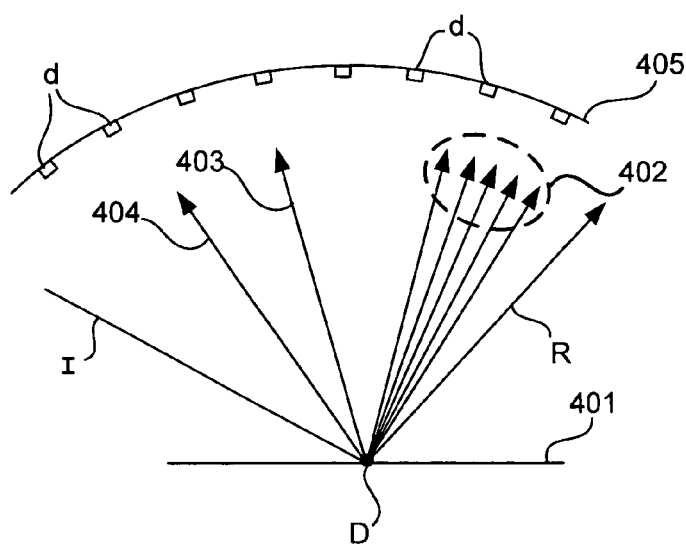
FIGS. 4(a) and 4(b) are simplified side and top schematic views of a light distribution induced by scattering from a surface.
Figure 4B:
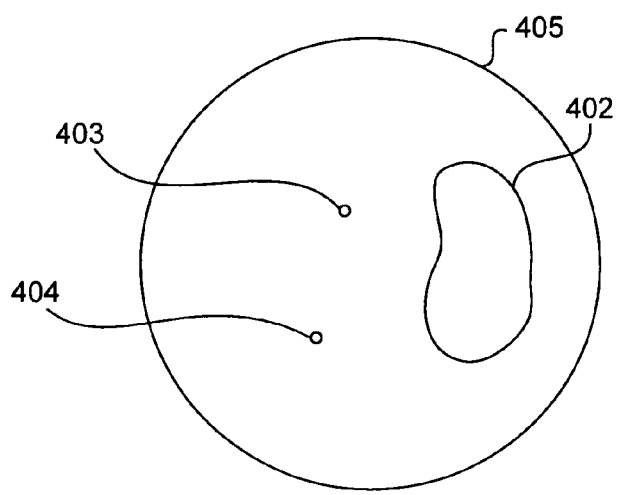
Figure 4C:
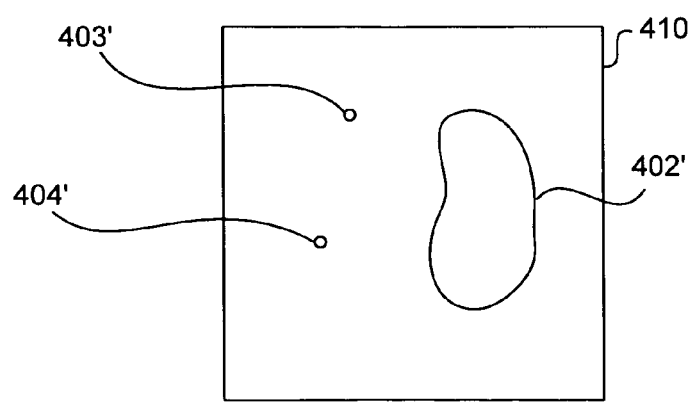
FIG. 4(c) is simplified two-dimensional mapping image corresponding to the scattering pattern depicted in FIGS. 4(a) and 4(b).

FIGS. 4(a), 4(b), and 4(c) are schematic depictions of various aspects of a light scattering pattern generated by the illumination of an un-patterned surface. FIG. 4(a) is similar to FIG. 2(b) in that an incident light beam I is used to illuminate an un-patterned wafer 401. The light is scattered 402, 403, 404 and is detected by a plurality of detectors d mounted hemispherically 405 around the wafer 401. In the depicted illustration the wafer 401 has a defect D that induces scattering. Much of the scattering is still in accordance with the ordinary scattering pattern 402 generated by the surface of wafer 401 in the absence of defects. However, the defect also causes scattering that results in scattered light beams 403 and 404. FIG. 4(b) is a simplified schematic top-down view of the light scattering pattern as the scattered light impinges on the plurality of detectors mounted hemispherically 405 around the wafer 401. This view provides some sense of the three-dimensional scattering pattern showing the ordinary scattering pattern 402 and the defect induced scattered light beams 403 and 404. This light scatter distribution can be mapped to a two-dimensional image using a variety of sensors. FIG. 4(c) depicts one example of such a two-dimensional mapping image 410. A portion of the mapping includes a light cluster 402' associated with the ordinary scattering pattern 402 and other portions of light 403', 404' associated with the defect scatter 403, 404. Thus, the ordinary scattering pattern can be identified. If it were possible to remove the light cluster 402' associated with the ordinary scattering pattern 402 from the image 410 the SNR could be substantially improved and the sensitivity of any associated surface inspection tool would be improved.

Figure 5:
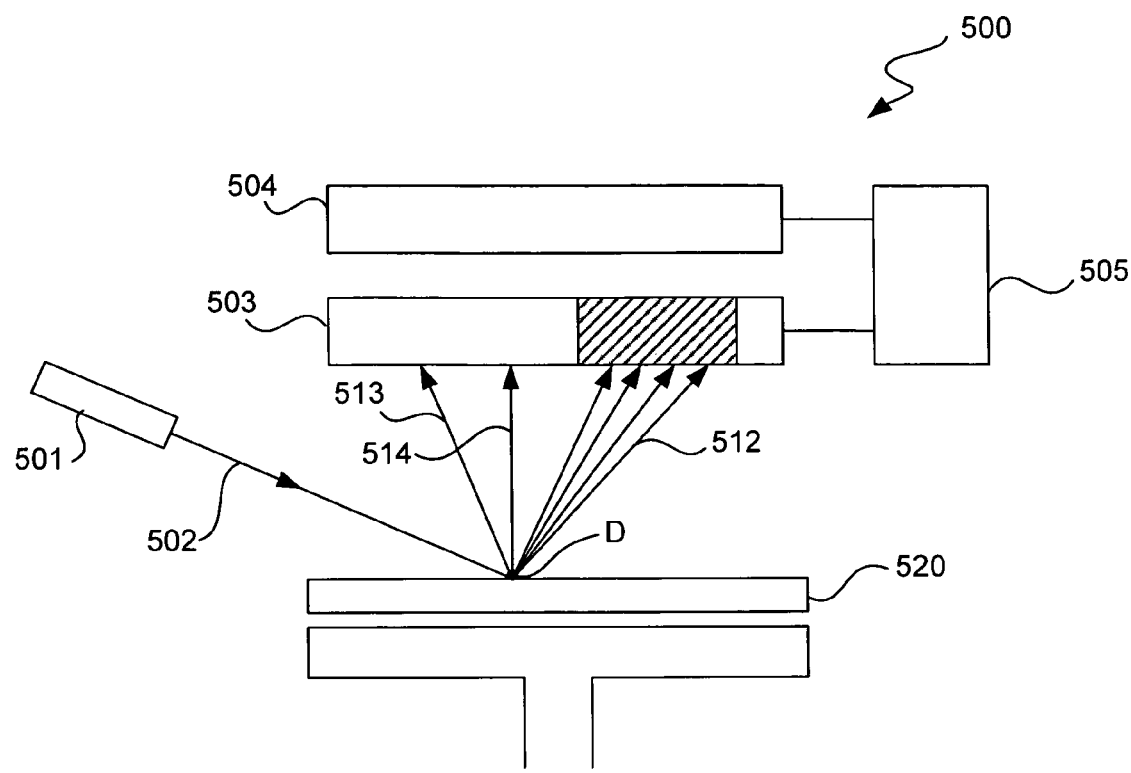
FIG. 5 is a block diagram showing aspects of a generalized apparatus constructed in accordance with the principles of the invention.

One simplified schematic depiction of a generalized apparatus constructed in accordance with the principles of the invention is depicted in FIG. 5. The apparatus 500 of FIG. 5 includes an illumination source 501, a programmable light selection element 503, a light detection element 504, and electronic circuitry 505 for analysis, processing, and control in the apparatus. The illumination source 501 is for producing an incident light beam 502 that is directed onto a workpiece 520 (e.g., an un-patterned wafer). Commonly, the illumination source 501 is a laser. However, other coherent sources can advantageously be used, for example, filtered lamps can be used. Filtered Hg (mercury) and Xe (xenon) lamps provide particularly satisfactory illumination sources. The workpiece is scanned so that the desired portions of the surface can be inspected. Commonly, the workpiece is placed on a movable support that moves the workpiece 520 so that it can be scanned. In one implementation the workpiece 520 is rotated and translated to affect a spiral inspection pattern. Other scanning regimes and approaches known to those having ordinary skill in the art can be used. Spiral scanning is preferred because an entire 300 mm wafer can be scanned in about 15 seconds. During scanning light is scattered from the surface of the workpiece 520. As depicted here, the light is scattered by a defect D on the workpiece 520. The resulting light distribution includes the ordinary scattering pattern (indicated by the many arrows of 512) of the surface and scattering caused by the defect 513, 514. The programmable light selection element 503 is constructed such that the scattering caused by the defect 513, 514 is selectively directed onto the light detection element 504 where it is detected, processed, and analyzed to (among other things) detect and categorize defects. Additionally, the light in the ordinary scattering pattern 512 is substantially prohibited from reaching the light detection element 504 (abstractly depicted by the cross-hashed lines in the light selection element 503). Thus, the light detection element 504 measures light scattered in the absence of substantially all of the light from the ordinary scattering pattern. This optical signal is then processed by the electronic circuitry 505 to identify and categorize the defects. The inventors contemplate that a wide range of light detection devices can be employed as a light detection element 504 in accordance with the principles of the invention. Preferably, the light detection element 504 is a light sensitive array type detector (e.g. a charge-coupled device (CCD)) that can form two-dimensional images of the received light. Many other types of devices can also be used, including, but not limited to, CMOS arrays, multi-cathode PMT's, photodiode arrays, and other array photodetectors known to persons having ordinary skill in the art. Moreover, a cluster (or distribution) of discrete photodetectors can also be used if desired. Additionally, the inventors contemplate embodiments where single discrete photodetector elements can be employed as the light detection element 504. Examples of such single discrete photo-sensitive detector devices include, but are not limited to photo-multiplier tubes, a photodiodes, avalanche photodiodes, as well as other similar devices.

Figure 6A:
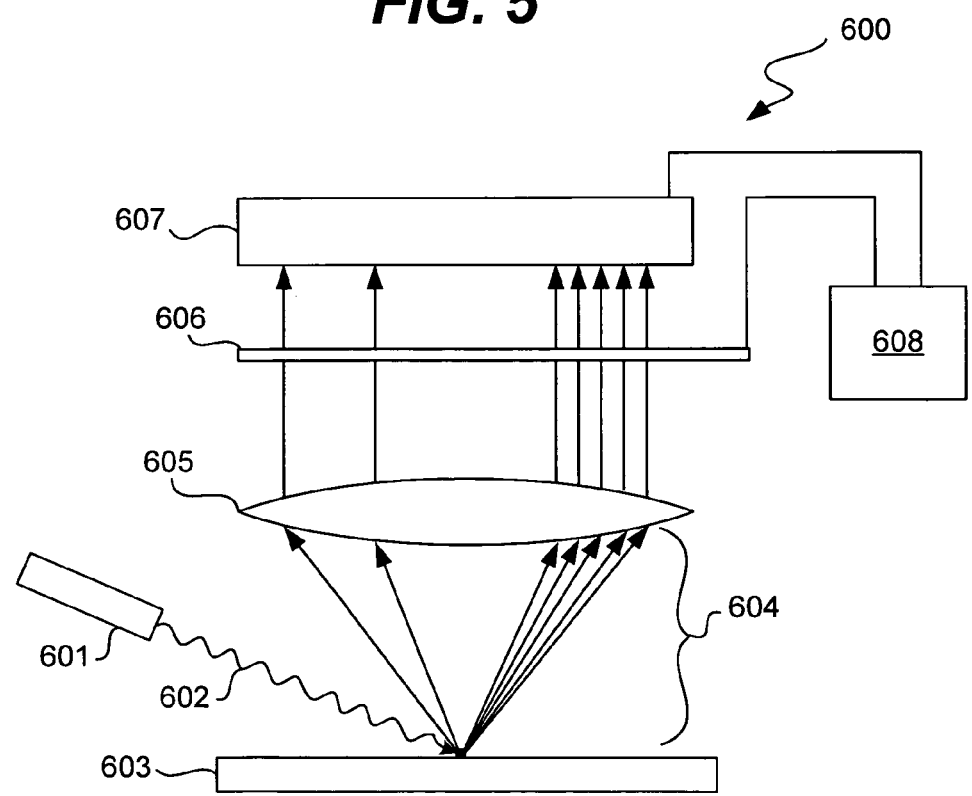
FIGS. 6(a)–6(c) are simplified schematic cross-sectional views of one apparatus embodiment of the invention showing aspects of selective filtering operation. Also, depicted is a two-dimensional image of the light scattered from the surface and detected by the apparatus.
Figure 6B:
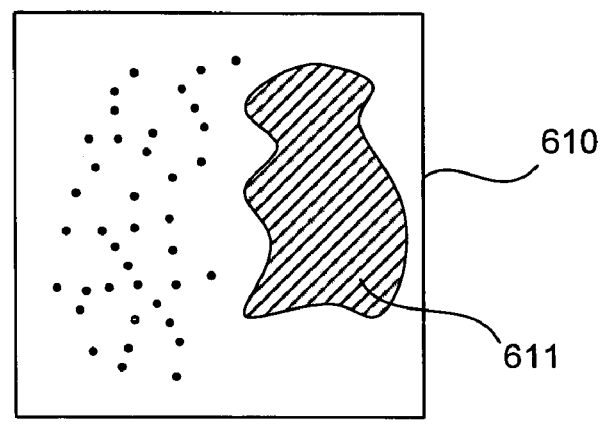
Figure 6C:
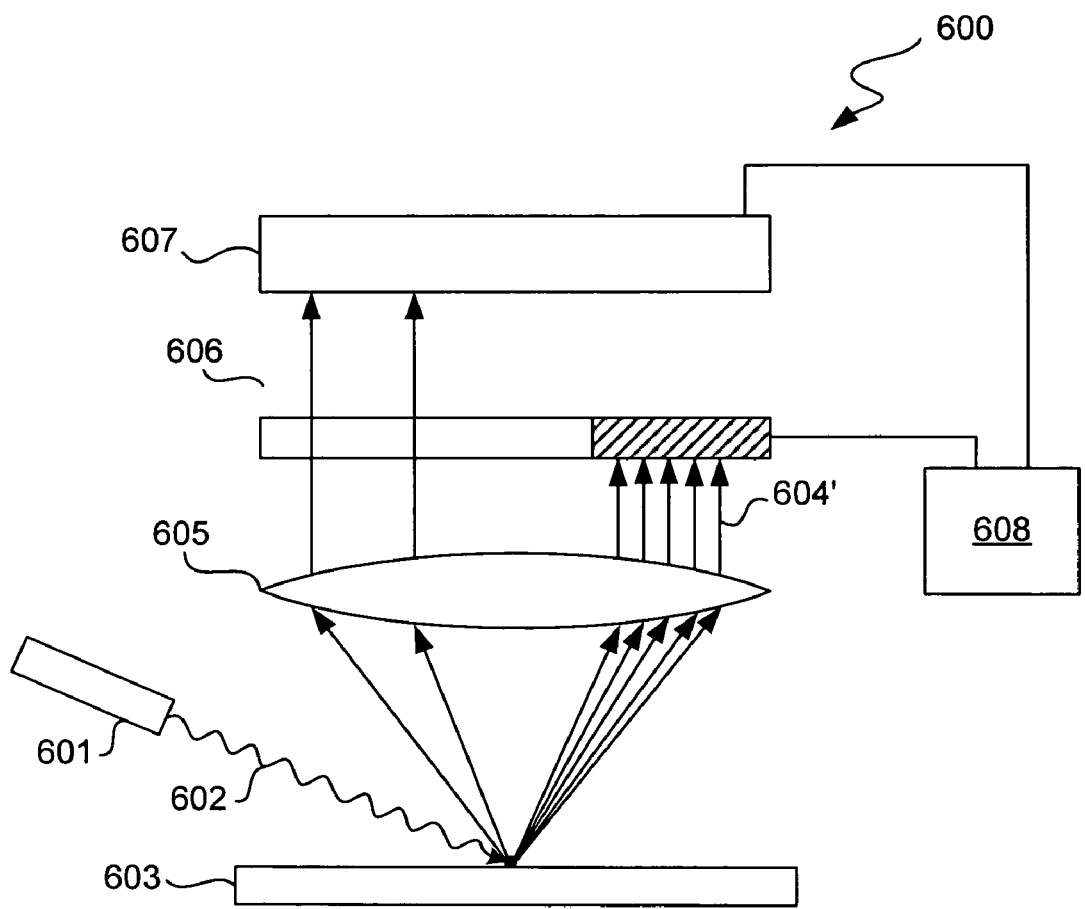

The functioning of such a device is best described with respect to the following illustrative embodiments and examples. FIGS. 6(a) and 6(c) are simplified depictions of one embodiment constructed in accordance with the principles of the invention. FIG. 6(b) depicts a sample light distribution pattern detected by a detector during scanning. Referring now to FIG. 6(a), the apparatus 600 includes an illumination source 601 that projects a light beam 602 onto the surface 603 being inspected. Light is scattered from the surface in a distribution pattern 604. The light passes through an optical element 605 (e.g., a lens element) and onto a programmable light selection array. In this embodiment, the programmable light selection array is a programmable filter array 606 is positioned to receive the scattered light. The programmable filter array 606 includes an array of individual filter elements that can be selectively activated or deactivated in order to selectively block or transmit scattered light through selected portions of the filter array 606. Such filter arrays can include, but are not limited to LCD filter arrays and selectively polarizable filter arrays (polarizers) that block or transmit light based on the polarity of the received light. Additionally, many other types of filter arrays known to persons having ordinary skill in the art can be used. A control element (which can optionally form part of the electronic circuitry 608) controls the selective activation and deactivation of the filter elements. As depicted in FIG. 6(a) the control element activates (or deactivates) the filter elements of the filter array 606 such that all the scattered light 604 is transmitted through the filter array 606 where it is received by a light detection element 607. Preferably, the light detection element 607 is a light sensitive array type detector (e.g. a charge-coupled device (CCD)) that can form two-dimensional images of the received light. Many other types of devices can also be used, including, but not limited to, CMOS arrays, multi-cathode PMT's, photodiode arrays, and other array photodetectors known to persons having ordinary skill in the art. Moreover, a cluster (or distribution) of discrete photodetectors can also be used if desired. Additionally, the inventors contemplate embodiments where single discrete photodetector elements can be employed as the light detection element 607. The desired portions of the surface 603 are then scanned to obtain an overall light distribution pattern for the surface. Keeping in mind that most (at least 99.9%) of the surface is free of defects most of the light distribution pattern is associated with the ordinary scattering pattern for the surface 603. An example light distribution is shown by image 610 produced by light detection element 607 shown in FIG. 6(b). The majority of the light (e.g., more than about 99.9%) is clustered in the ordinary scattering pattern 611. Most of the remaining scattered light is scattered from defects. This image data is then processed by processor elements of the electronic circuitry 608. The circuitry 608 can then determine which filter elements to be activated (deactivated) in order to filter out the ordinary scattering pattern 611. Many different types of microelectronic devices can be used to facilitate such filtering. Such devices include, but not limited to DSP's (digital signal processors), ASIC's (application specific integrated circuits), as well as other microprocessor devices. Additionally, many different types of algorithms or signal processing techniques known to persons having ordinary skill in the art can be used to determine which portions of the image are associated with the ordinary scattering pattern. As a result, selected individual filter elements of the filter array 606 are activated/deactivated to block the transmission of the ordinary scattering pattern onto the light detection element 607.

FIG. 6(c) is a simplified schematic depiction of the operation of the filter elements of the filter array 606. The control element of the electronic circuitry 608 selectively engages the filter elements of the of the filter array 606 in order to selectively block the transmission of the ordinary scattering pattern 604' (as depicted by the cross-hashing on the filter array 606). As a result only scattered light caused by defects reaches the light detection element 607 where it is detected and converted into a defect signal that is received by the defect analysis circuitry (which can optionally form part of the electronic circuitry 608) and processed to identify and categorize defects of the surface 603. This process of detecting the ordinary scattering pattern can be conducted for each wafer so inspected. Also, the ordinary scattering pattern can be determined for a group of similar wafers (e.g., a series of wafers at the same step an a fabrication process). Alternatively, the ordinary scattering pattern can be mathematically determined from a database characterizing a surface using an optical modeling program that can calculate the expected light scattering distribution for a surface. Many such modeling programs are well known to persons having ordinary skill in the art. It should be noted that many other light beam shaping devices can be used in place of the lens element 605. Examples include without limitation, parabolic and elliptical reflectors. Additionally, the reader is reminded that the depicted embodiment is a simplified implementation, and many other optical elements, or combinations of optical elements, can be used to practice the principles of the invention.

Figure 6D:
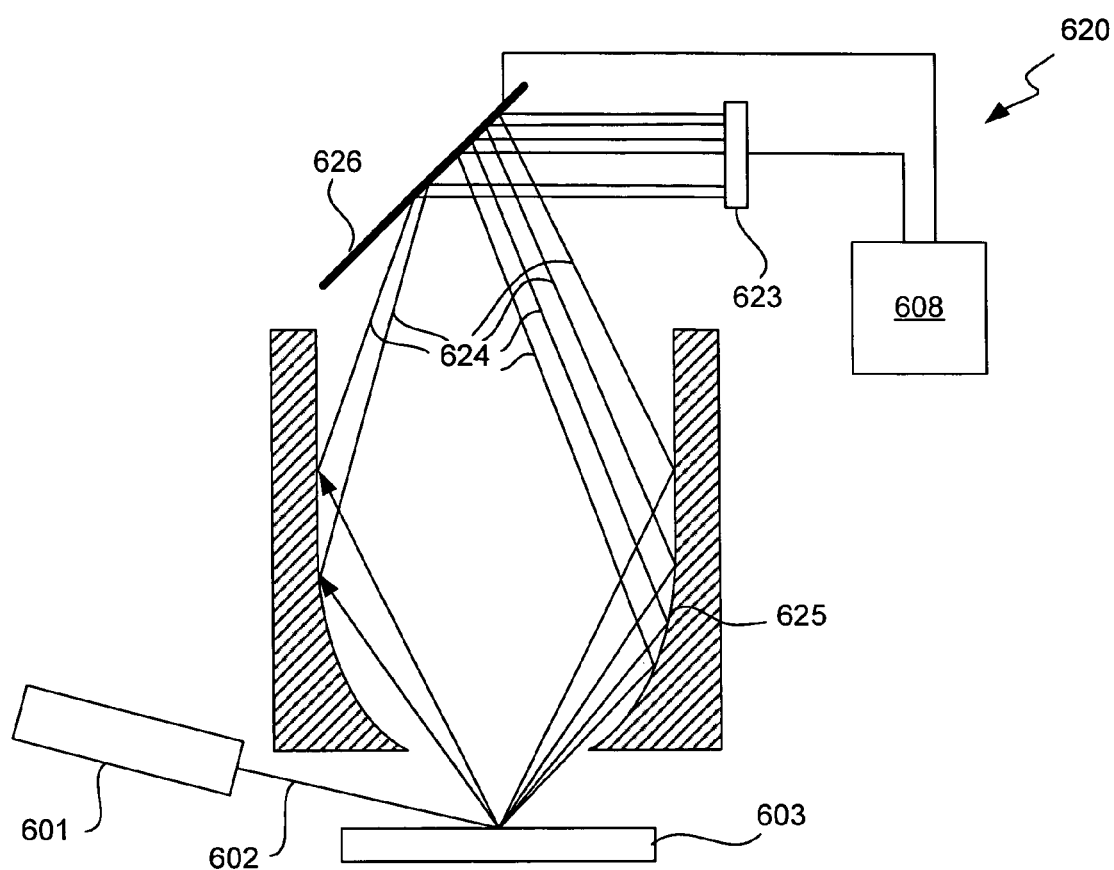
FIGS. 6(d)–6(g) are simplified schematic cross-sectional views of another apparatus embodiment of the invention showing aspects of selective light selection using reflector arrays. Also, depicted is a two-dimensional image of the light scattered from the surface and detected by the apparatus.
Figure 6E:
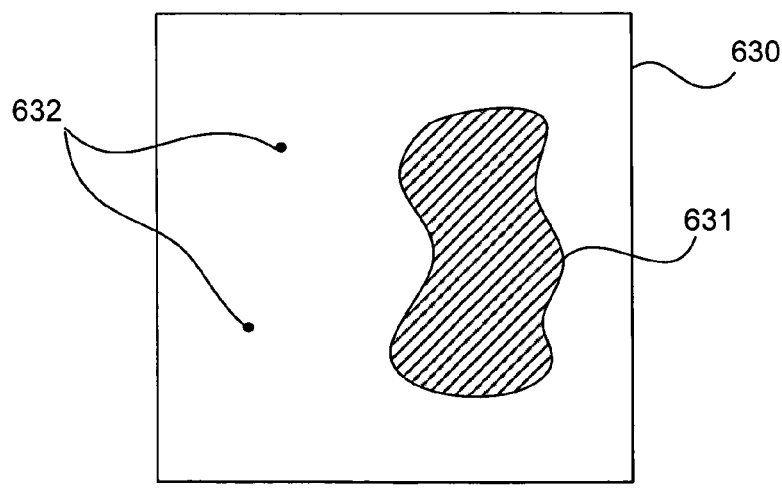
Figure 6F:
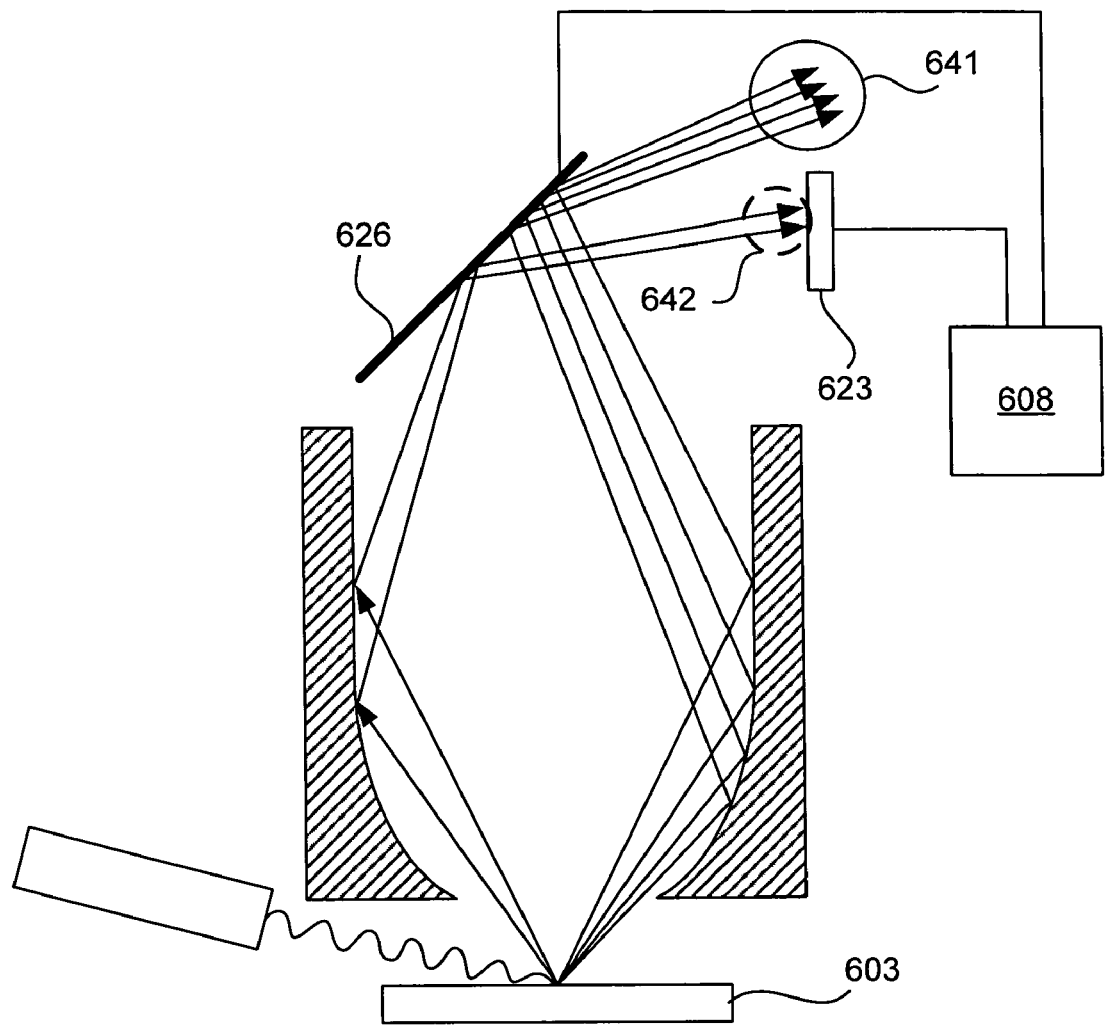

FIGS. 6(d)–6(g) describe further illustrative embodiments. FIGS. 6(d) and 6(f) depict the mode of operation of another embodiment constructed in accordance with the principles of the invention. FIG. 6(e) depicts a sample light distribution pattern detected by a detector during scanning. Referring now to FIG. 6(d), the apparatus 620 includes an illumination source 601 that projects a light beam 602 onto the surface 603 being inspected. Light is scattered from the surface in a distribution pattern 624. The light passes through an optical element 625 (e.g., a reflector element) and onto a programmable light selection array. In this embodiment, the programmable light selection array is a programmable reflector array 626 is positioned to receive the light distribution pattern 624. The programmable reflector array 626 includes an array of individual reflector elements that can be selectively activated or deactivated in order to selectively direct selected portions of the scattered light onto the light detection element 623. Such reflector arrays can include, but are not limited to mirror arrays such as MEMS (micro-electro-mechanical system) mirror arrays that can be actuated to selectively direct incident light beams in different directions. In particular, unwanted light can be directed away from the light detection element 623. A control element (which can optionally form part of the electronic circuitry 608) controls the selective activation and deactivation of the reflector elements. As depicted in FIG. 6(d) the control element activates (or deactivates) the reflector elements of the programmable reflector array 626 such that all the scattered light 624 is reflected onto the light detection element 623. As with the previously discussed light detection elements (e.g., 607 of FIGS. 6(a)–6(c)), the light detection element 623 is a light sensitive array type detector (e.g. a charge-coupled device (CCD)) that can form two-dimensional images of the received light. Also as before, many other types of devices and detector arrangements can also be used, including, but not limited to, distributions of discrete photodetector devices, CMOS arrays, multi-cathode PMT's, photodiode arrays, and other array photodetectors known to persons having ordinary skill in the art. The desired portions of the surface 603 are then scanned to obtain an overall light distribution pattern for the surface. FIG. 6(e) depicts an example light distribution produced by light detection element 623 (which is generally similar to that depicted in FIG. 6(b)) and shown as image 630. As before, the majority of the light (e.g., more than about 99.9%) is clustered in the ordinary scattering pattern 631.

Most of the remaining scattered light is scattered from defects and is schematically depicted here by light spots 632. This image data is then processed by processor elements (which can be included as part of the electronic circuitry 608 or optionally included as separate elements).

As depicted in FIG. 6(f), the circuitry 608 can then determine which reflector elements are to be selectively activated/deactivated in order to selectively direct light of the ordinary scattering pattern 641 (depicted by the circled arrows) away from the light detection element 623. As the ordinary scattering pattern 641 is directed away from the light detection element 623, the light associated with the defects 642 (depicted by the dashed circled arrows) is selectively directed onto the light detection element 623 where it is detected and can be used for surface analysis. The circuitry 608 can then determine which reflector elements are to be selectively activated/deactivated in order to direct light of the ordinary scattering pattern 641 away from the light detection element 623. As previously disclosed, many different types of electrical and electronic devices can be used to facilitate the selective directing of light onto an appropriate detection device. Also, as disclosed many different types of algorithms or signal processing techniques known to persons having ordinary skill in the art can be used to determine which portions of the image are associated with the ordinary scattering pattern. As a result, selected individual reflector elements of the reflector array 626 are activated/deactivated to direct selected portions of the scattered light onto the light detection element 623.

Figure 6G:
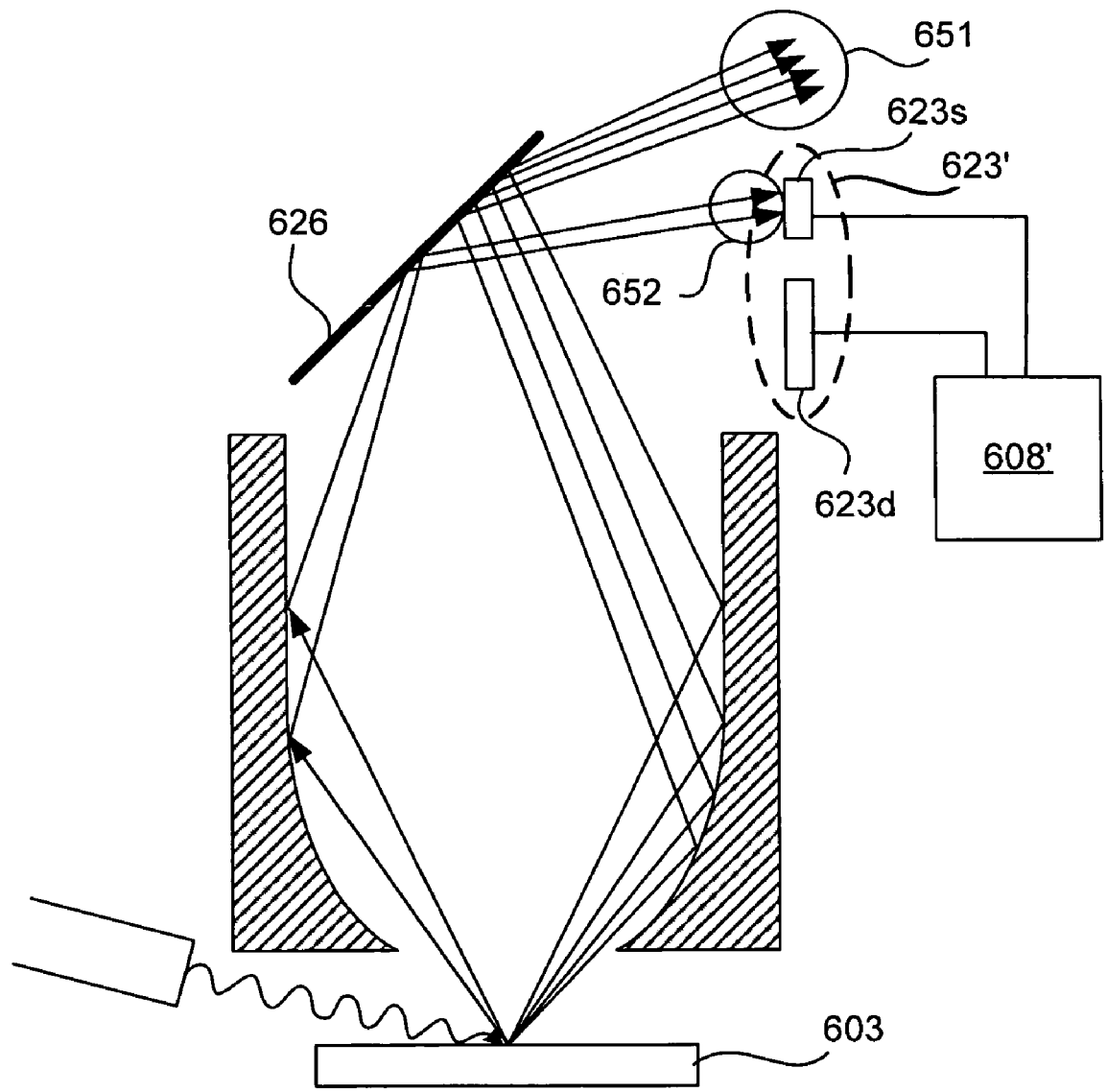

As depicted in FIG. 6(g), in one alternative approach, the light detection element 623' includes both a photodetector 623d and a photosensor 623s. The photodetector 623d is a detector that can generate two-dimensional images of the detected scattering pattern. Typically, such a photodetector 623d comprises a photodetector array (as described previously hereinabove). The inventors also contemplate a photodetector 623d comprising a plurality of photo-sensitive devices distributed in a configuration that collects the scattered light from the workpiece. The light detection element 623' also includes a photosensor 623s. The photosensor 623s is commonly (but not exclusively) a discrete photodetector device. As before, the circuitry 608 determines which portion of the scattered light is associated with the ordinary scattering pattern 651 (depicted here in the labeled circle). The reflector elements are to be selectively activated/deactivated in order to direct light of the ordinary scattering pattern 651 away from the photosensor 623s. Additionally, the circuitry 608 selectively activates/deactivates reflector elements of the reflector array 626 in order to selectively direct light 652 onto the photosensor 623s where it is detected and used to characterize the surface 603. The photosensor 623s can comprise a discrete photosensor element (e.g., a photomultiplier tube (PMT)) to detect the light scattered from the inspection surface. Alternatively, the photosensor 623s can include another device(s) capable of generating a two-dimensional image of the received light.

In another associated embodiment, the device depicted in FIG. 6(g) can be used to direct the light of the ordinary scattering pattern 651 onto the photodetector 623d. Thus, if desired the ordinary scattering pattern 651 can be continuously monitored during inspection.

In yet another embodiment even more detectors can be used. For example, as depicted in FIGS. 7(a) and 7(b), a KLA-Tencor Model SP1 darkfield inspection tool (produced by KLA-Tencor Corporation of San Jose, Calif.) can be modified to incorporate the principles of the present invention.

Figure 7A:
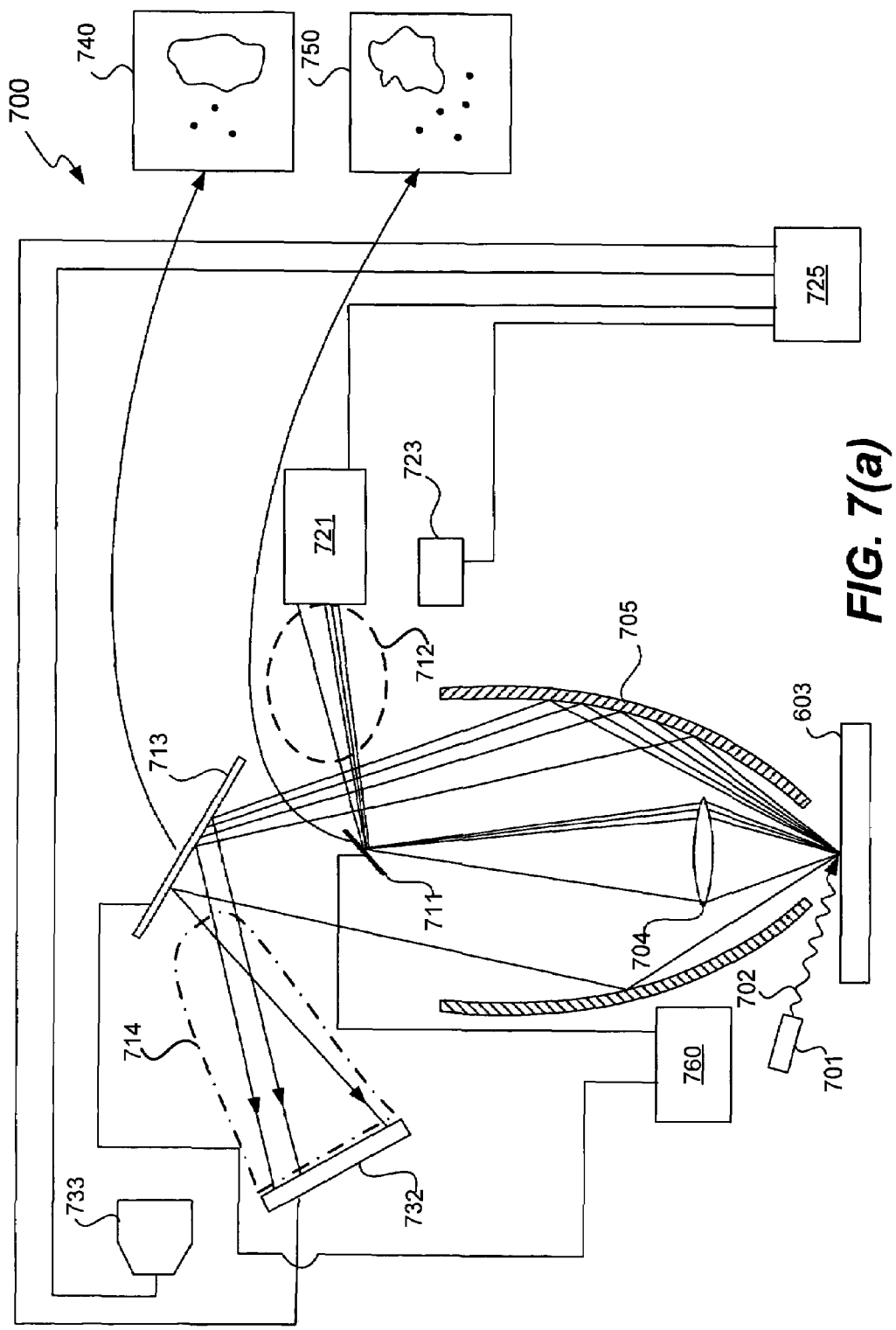
FIGS. 7(a) and 7(b) are simplified schematic cross-sectional views of another apparatus embodiment of the invention showing aspects of selective light selection using reflector arrays. Also, depicted is are two-dimensional images of light scattered from the surface and detected by the apparatus.
Figure 7B:
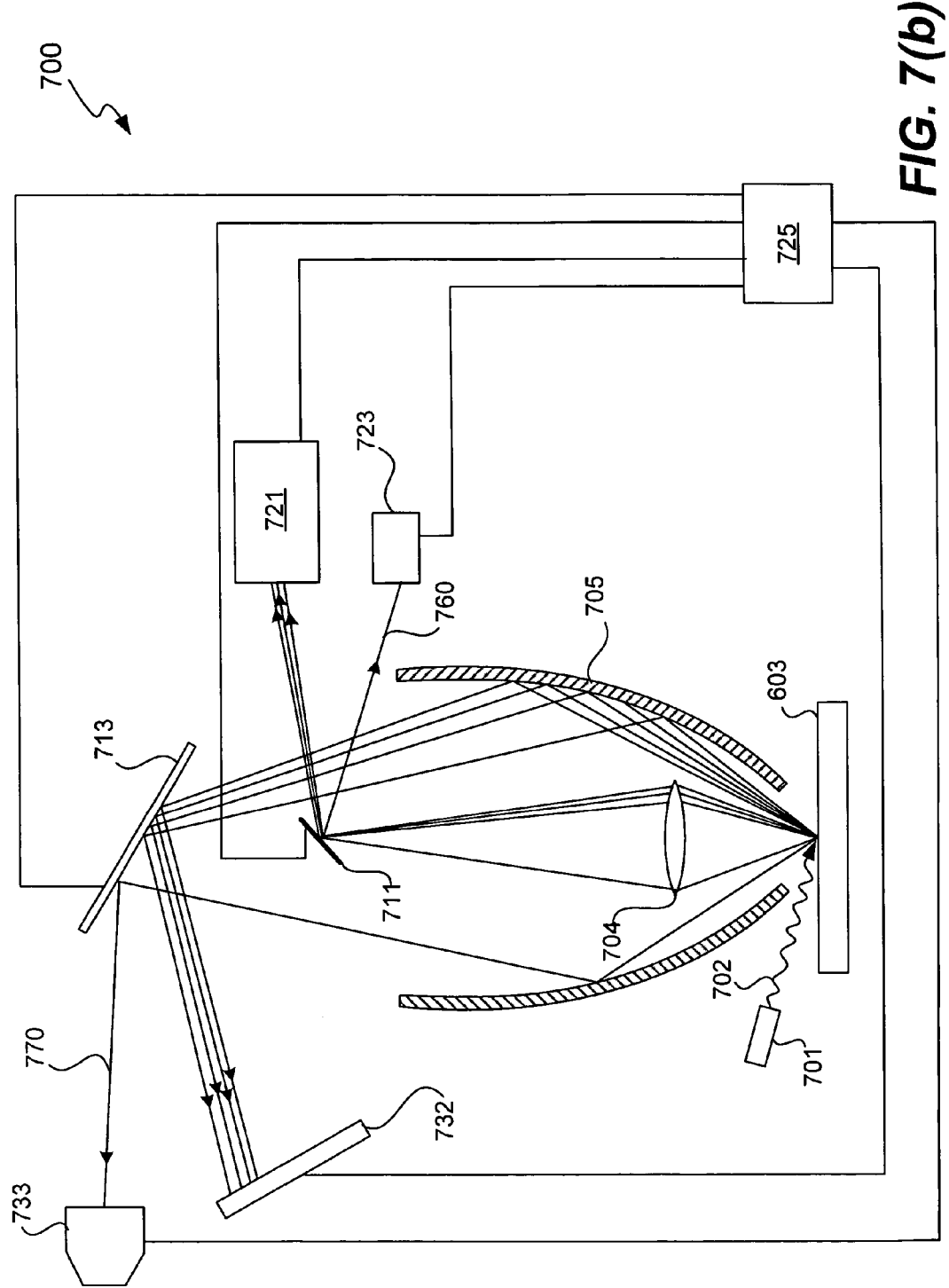

FIG. 7(a) depicts a darkfield inspection apparatus 700 in accordance with the principles of the invention. The apparatus 700 includes an illumination source 701 that projects a light beam 702 onto the surface 603 being inspected. As previously described, light is scattered from the surface in a scattering distribution pattern.

The scattered light passes through a first optical element 704 (e.g., a lens or group of lenses) or onto a second optical element 705 (e.g., a reflector element). A first programmable light selection array receives the light passing through the first optical element 704 and directs the light onto a photodetector element 721. In this embodiment, the first programmable light selection array includes, but is not limited to, a first programmable reflector array 711 which directs the scattered light 712 (the light in the dashed oval) onto a first photodetector array 721. A with the previously described embodiments, the first photodetector array 721 (e.g. a charge-coupled device (CCD)) is configured so that it can form two-dimensional images of the received light. Also, as before, many other types of devices and detector arrangements can also be used, including, but not limited to, distributions of discrete photodetector devices, CMOS arrays, multi-cathode PMT's, photodiode arrays, and other array photodetectors known to persons having ordinary skill in the art.

Additionally, the scattered light interacts with the second optical element 705 (depicted here as a reflector element). The light is reflected by the second optical element 705 and onto a second programmable light selection array. In this embodiment, the second programmable light selection array is a second programmable reflector array 712. The depicted programmable light selection array includes, but is not limited to, a second programmable reflector array 713 which directs the scattered light 714 (the light in the dotted dashed encircled area) onto a second photodetector array 732. A with the previously described embodiments, the second photodetector array 732 (e.g. a charge-coupled device (CCD)) is configured so that it can form two-dimensional images of the received light. Also, as before, many other types of devices and detector arrangements can also be used, including, but not limited to, distributions of discrete photodetector devices, CMOS arrays, multi-cathode PMT's, photodiode arrays, and other array photodetectors known to persons having ordinary skill in the art.

Thus, during scanning, the first photodetector array 721 forms a first set of images 740 of the scattering pattern caused by the surface 603. Also, the second photodetector array 732 forms a second set of images 750 of the scattering pattern caused by the surface 603. The ordinary scattering pattern 741 of the first set of images 740 can be empirically determined using the first set of images 740. Additionally, the ordinary scattering pattern 751 for the second set of images 750 can be determined using the second set of images 750. Using the principles of the present invention as described previously, the respective ordinary scattering pattern 741, 751 can be used to selectively identify the scattered light generated by defects in the surface 603. Using, the first programmable reflector array 711 and the second programmable reflector array 712 respectively, associated defect signals can be directed into appropriate photosensors for detection (e.g., See, FIG. 7(b)). Also, as previously described, the electronic circuitry 725 receives data from the photodetectors 721, 732 and uses such data to selectively activate the light selection elements of the programmable light selection arrays 711, 713. Examples of such light selection elements of the programmable light selection arrays include, but are not limited to, filter elements of the programmable filter arrays and reflector elements of the programmable reflector arrays.

With further reference to FIG. 7(b), the apparatus 700 selectively directs the scattered light 760, 770 caused by defects of the surface 603 onto the associated photosensor 723, 733. For example, the scattered light 760 passing through the first optical element 704 is directed, by the first reflector array 711, onto the first photosensor 723. Correspondingly, the scattered light 770 from the second optical element 705 is directed, by the second reflector array 713, onto the second photosensor 733. Also, the ordinary scattering patterns 761, 771 remain directed on the associated photodetectors 721, 732 respectively. Thus, the defect containing signals 760, 770 are directed onto photosensors 721, 733 which each produce electrical signals that are received by electronic circuitry 725 and used to identify and categorize defects in the surface 603. Additionally, such signals can be used to otherwise characterize the surface 603.

It should be apparent to those having ordinary skill in the art that other configurations and implementations can be used to implement an apparatus in accordance with the principles of the invention. For example, the configurations and optical elements can be altered to incorporate different types of programmable light selection array (e.g., filter arrays). Such changes and modifications are contemplated by the inventors and, using the teachings described herein, require no undue experimentation on the part of a person having ordinary skill in the art in order to use. As previously described, the configurations and optical elements can be altered to incorporate different types of programmable light selection array (e.g., filter arrays). Such changes and modifications are contemplated by the inventors and require no undue experimentation on the part of a person having ordinary skill in the art.

Figure 8:
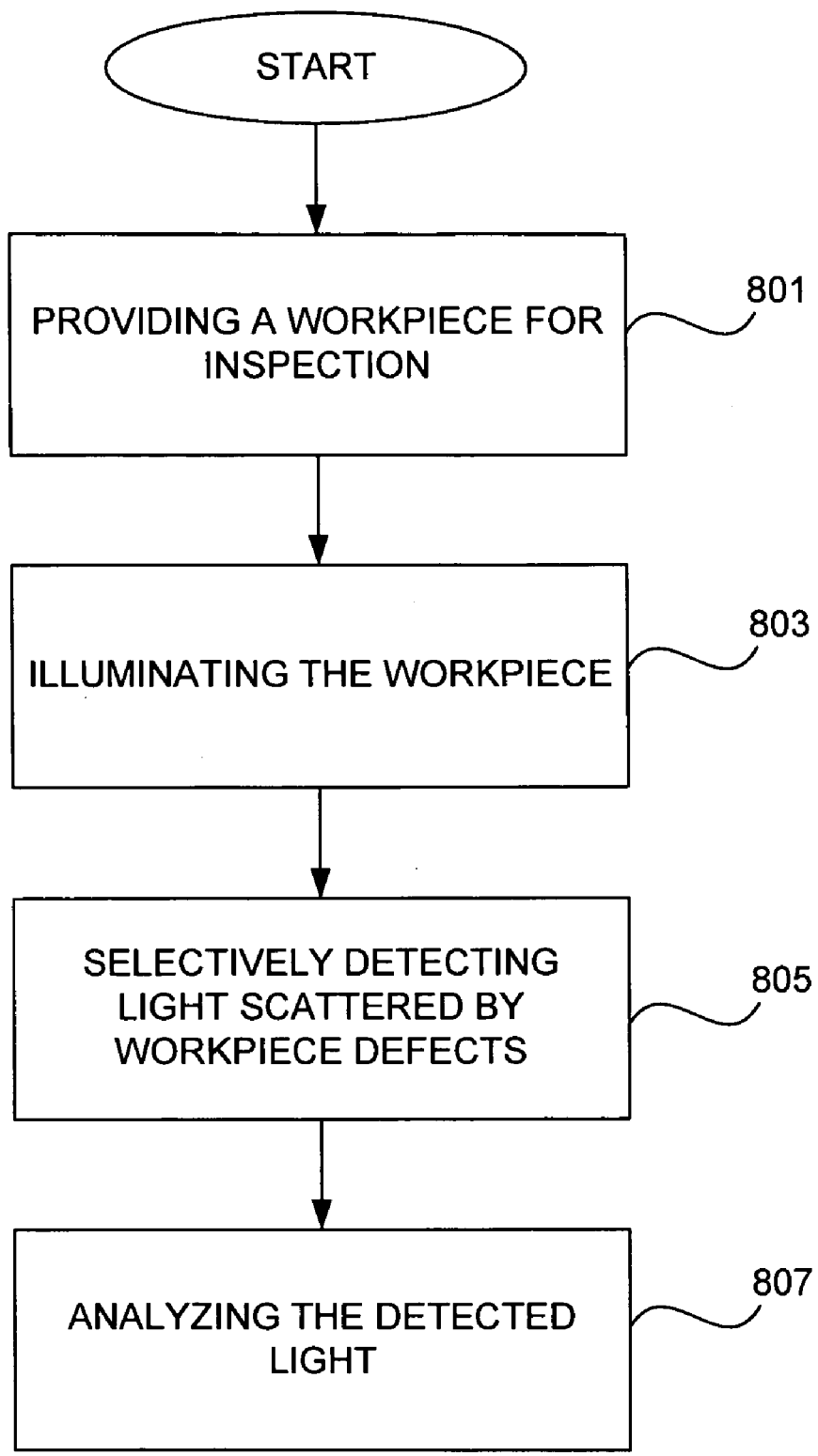
FIG. 8 is a flow diagram depicting a method embodiment in accordance with the principles of the present invention.

FIG. 8 is a flow diagram illustrating an embodiment of a process for inspecting a surface of a workpiece in accordance with the principles of the present invention. Such a surface inspection method begins by providing a workpiece for inspection (Step 801). Commonly, such workpieces comprise semiconductor wafers. Although such methods can be applied to patterned wafers, the teachings of this patent have particular utility when applied to un-patterned wafers and wafers having un-patterned surface layers (both cases being generally referred to herein as un-patterned wafers). Such un-patterned wafers are defined as wafers having no defined semiconductor device patterns formed thereon in accord with a semiconductor fabrication scheme. Such wafers can include silicon (Si) wafers and may also include other types of wafers including, but not limited to, silicon germanium (SiGe) wafers or gallium arsenide (GaAs) wafers. Additionally, un-patterned wafers having un-patterned layers of material formed thereon are very well suited to inspection using methods disclosed herein. For example, an un-patterned silicon wafer can have an un-patterned metallization layer formed thereon. Such a layer can be formed of, for example, aluminum and copper as well as other metals or compounds. Such un-patterned layers can be formed of many other materials and are not intended to be limited to any specific materials disclosed herein. The inventors point out that the ordinary scattering pattern generated by non-defect portions of the surface can vary substantially from these previously depicted configurations. Salient examples of such variation are demonstrated by epitaxially grown silicon wafers and silicon germanium wafers. Also, distinct scattering patterns have been observed for surfaces having strained silicon surface layers. Additionally, distinct scattering patterns have been observed for surfaces having unpatterned metal surface films, unpatterned polysilicon films, unpatterned copper films. Additionally, surfaces that have been polished or otherwise processed in such a manner as to result in a rough or textured surface can produce such deviations from the depicted "ordinary" scattering pattern. Such wafers are loaded into an appropriate machine and then inspected. Inspection begins with illuminating the workpiece to produce scattered light (Step 803). The wafer can be scanned (e.g., using a spiral or other inspection pattern) to produce scattered light. The scattered light includes light scattered from defects in the workpiece (also referred to as defect scatter) and includes light scattered from non-defect portions of the workpiece. The light scattered from non-defect portions of the workpiece generates an ordinary scattering pattern for the workpiece. Such scattering patterns are well discussed herein above. FIGS. 6(b) and 6(e) depict typical examples of a silicon wafer scattering pattern.

Figure 9C:
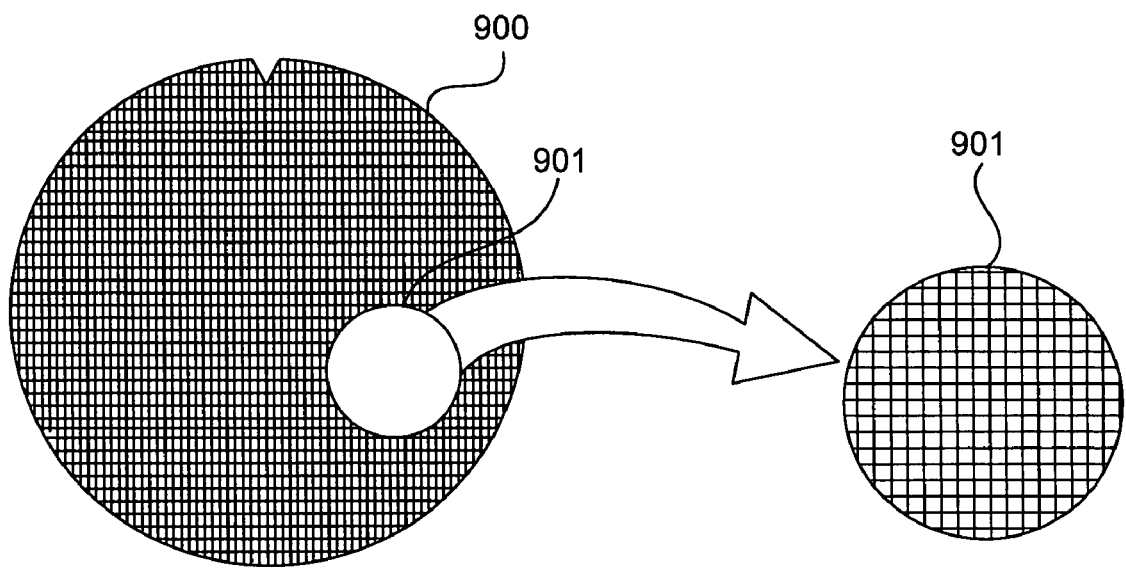
Figure 9C:
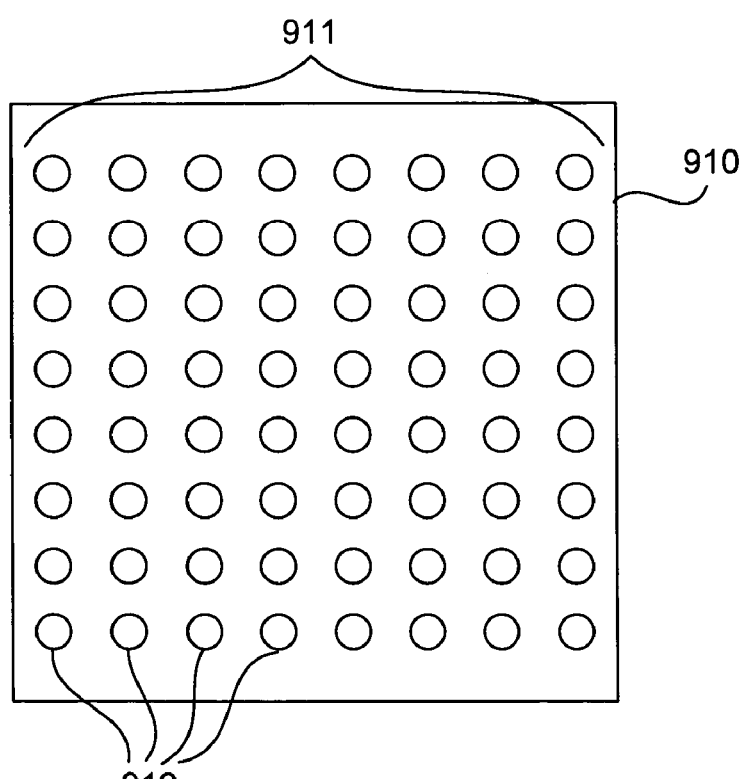

For example, FIG. 9(a) is a simplified schematic depiction of an un-patterned epitaxial silicon 300 mm wafer 900. The wafer 900 has an epitaxially grown surface. Portion 301 is shown in close-up in FIG. 9(b). The depicted un-patterned wafer surface has a minute cross-hatched pattern characteristic of an epitaxially grown silicon crystal structure. Silicon germanium wafers also have an inherent crystalline structure. These inherent crystal structures influence the ordinary scattering pattern of the wafer in the absence of defects. Instead of the light clustering as shown, for example, in FIGS. 6(b) and 6(e), a different characteristic scattering pattern is observed. Because, such characteristic scattering patterns are well-known by those having ordinary skill in the art, they can be incorporated into the principles of the present invention. One example, schematically depicted in FIG. 9(c), contains a simplified image 910 of an ordinary scattering pattern 911 taken from an illuminated epitaxially grown silicon wafer surface. The ordinary scattering pattern of such a wafer also contains patterns of light and dark regions characteristic of the wafer surface. Light spots 912 define the ordinary scattering pattern. Such scattering patterns can be modeled using algorithms, computer programs, and associated methodologies generally constructed for such purposes. Many such methodologies are known to persons having ordinary skill in the art and can be implemented for such purposes. Once the ordinary scattering pattern of the wafer is identified, apparatuses (such as those disclosed herein) can be used to selectively exclude the ordinary scattering pattern from the measured signal by using programmable light selection devices as disclosed generally herein (as well as similar devices).

Returning to the flow diagram of FIG. 8, after illumination the light scattered by defects (defect scatter) can be selectively detected (Step 805). As described above, the defect scatter can be identified by a determination of the ordinary scattering pattern. Which generally proceeds by detecting the scattered light and then determining which of the scattered light comprises the ordinary scattering pattern of the wafer. After identifying the ordinary scattering pattern, the ordinary scattering pattern is selectively excluding from detection. Thus, the remaining light comprises light scattered by defects, thereby selectively detecting the defect scatter. This selectively detected defect scatter is then analyzing to characterize the workpiece surface (Step 807). Signal processing circuitry and surface analysis software can be used to analyze the detected scattering lights. Defects can be identified, located, classified, or otherwise characterized. Moreover, the surface in general can be characterized using the detected scattered light.

It should be pointed out that the ordinary scattering pattern can be generated by scanning one wafer and then using the ordinary scattering pattern determined from that scan as the "baseline" optical signature for all similarly configured wafers. Additionally, because scanning is such a quick process (e.g., on the order of about 20 seconds) each wafer can be scanned individually to provide its own baseline optical signature (e.g., its own ordinary scattering pattern) and then defect detection analysis can be conducted. Each approach has its own advantages and will be used by an inspector to accomplish different goals. Additionally, as indicated previously, the ordinary scattering pattern can be determined by applying an optical modeling program to a database model of the wafer to be inspected. Such optical modeling programs can be used to process database information about a wafer to determine a theoretical light scattering profile for the wafer. This light scattering profile includes the ordinary scattering pattern for the wafer. Thus, the ordinary scattering pattern can be determined using a database modeling of the surface alone.

The present invention has been particularly shown and described with respect to certain preferred embodiments and specific features thereof. However, it should be noted that the above-described embodiments are intended to describe the principles of the invention, not limit its scope. Therefore, as is readily apparent to those of ordinary skill in the art, various changes and modifications in form and detail may be made without departing from the spirit and scope of the invention as set forth in the appended claims. Other embodiments and variations to the depicted embodiments will be apparent to those skilled in the art and may be made without departing from the spirit and scope of the invention as defined in the following claims. In particular, it is contemplated by the inventors that light selection arrays of the present invention can comprise many different types of light selection arraysbeyond the specifically disclosed filter and reflector arrays. Photodetectors and photosensors in accordance with the principles of the present invention can have a wide variety of shapes and can include photodetector arrays having curved surfaces. The inventors also contemplate a variety of reflector shapes (e.g., not limited to paraboloid and ellipsoid surfaces). Further, reference in the claims to an element in the singular is not intended to mean "one and only one" unless explicitly stated, but rather, "one or more". Furthermore, the embodiments illustratively disclosed herein can be practiced without any element, which is not specifically disclosed herein.

We claim:

1. A surface inspection apparatus comprising:
   an illumination source for directing a light beam onto a workpiece to generate scattered light that includes light scattered from defects of the workpiece and light scattered in accordance with the ordinary scattering pattern of the workpiece;
   a programmable light selection array positioned to receive light scattered from the workpiece and direct the light onto a first photodetector array;
   the first photodetector array is positioned to receive the light from the programmable light selection array and capable of translating the light into an associated electrical signal;
   circuitry for receiving the associated electrical signal and determining which portion of the light scattered from the workpiece comprises the ordinary scattering pattern of the workpiece;
   the programmable light selection array further selectively directs the light scattered from defects of the workpiece onto a photosensor where it is translated into an associated defect signal; and
   processing circuitry for receiving the defect signal and using it to conduct surface analysis of the workpiece.

2. The tool of claim 1 wherein the programmable light selection array comprises an array of reflector elements that are selectively enabled to direct the light scattered from the workpiece onto the photosensor.

3. The tool of claim 2 wherein array of reflector elements comprises an array of MEMS reflector elements.

4. The tool of claim 2 wherein selected reflector elements of the array of reflector elements are actuated so that light scattered from the defects in the workpiece is selectively directed onto the photosensor and so that the light scattered by the non-defect containing portions of the workpiece is not directed onto the photosensor.

5. The tool of claim 1 wherein the first photodetector array comprises at least two photodetector arrays and wherein the photosensor comprises at least two photosensors.

6. The tool of claim 1 wherein the workpiece comprises an un-patterned surface.

7. The tool of claim 6 wherein the un-patterned surface comprises a semiconductor wafer.

8. The tool of claim 6 wherein the un-patterned surface comprises a semiconductor wafer having at least one un-patterned layer of material formed thereon.

9. The tool of claim 6 wherein the workpiece comprises a semiconductor wafer having a surface formed by an epitaxial fabrication processes.

10. The tool of claim 6 wherein the workpiece comprises a semiconductor wafer formed using silicon germanium material.

11. The apparatus of claim 1 wherein the apparatus comprises a darkfield inspection tool.

12. The apparatus of claim 1 wherein the photosensor comprises a discrete photosensor element.

13. The apparatus of claim 12 wherein the photosensor comprises a plurality of discrete photo sensor elements.

14. The tool of claim 12 wherein the programmable light selection array comprises an array of reflector elements that are selectively enabled to direct the light scattered from the workpiece onto the photosensor.

15. The tool of claim 14 wherein array of reflector elements comprises an array of MEMS reflector elements.

16. The tool of claim 14 wherein selected reflector elements of the array of reflector elements are actuated so that light scattered from the defects in the workpiece is selectively directed onto the photosensor and so that the light scattered by the non-defect containing portions of the workpiece is not directed onto the photosensor.

17. The apparatus of claim 1 wherein the photosensor comprises a second photodetector array.

18. The tool of claim 17 wherein the programmable light selection array comprises an array of reflector elements that are selectively enabled to direct the light scattered from the workpiece onto the photosensor.

19. The tool of claim 18 wherein array of reflector elements comprises an array of MEMS reflector elements.

20. The tool of claim 18 wherein selected reflector elements of the array of reflector elements are actuated so that light scattered from the defects in the workpiece is selectively directed onto the photosensor and so that the light scattered by the non-defect containing portions of the workpiece is not directed onto the photo sensor.

21. The apparatus of claim 1 wherein the first photodetector array also operates as the photosensor.

22. The tool of claim 21 wherein the programmable light selection array comprises an array of filter elements that are selectively activated and deactivated to enable the light scattered from the workpiece to pass through the array of filter elements thereby directing the light scattered from the defects of the workpiece onto the photo sensor.

23. The tool of claim 22 wherein array of filter elements comprises an array of LCD filter elements.

24. The tool of claim 22 wherein array of filter elements comprises an array of selectively activatable polarizer elements that can filter by polarization.

25. The tool of claim 1 wherein the programmable light selection array comprises an array of reflector elements that are selectively enabled to direct the light scattered from the workpiece onto the photosensor.

26. The tool of claim 25 wherein array of reflector elements comprises an array of MEMS reflector elements.

27. The tool of claim 25 wherein selected reflector elements of the array of reflector elements are actuated so that light scattered from the defects in the workpiece is selectively directed onto the photosensor and so that the light scattered by the non-defect containing portions of the workpiece is not directed onto the photo sensor.

28. An surface inspection apparatus comprising:
an illumination source for directing a light beam onto a workpiece;
a programmable light selection array positioned to receive light scattered from the workpiece, the programmable light selection array for directing said light onto to a photodetector element and also capable of selectively directing selected portions of the light onto to a photosensor element;
the photodetector element being positioned such that it receives light from the programmable light selection array and translates said received light into an associated electrical signal;
processing circuitry for receiving and analyzing the associated electrical signal from the first photodetector element and thereby determining an ordinary scattering portion of the of the light scattered from the workpiece that is associated with an ordinary scattering pattern of the workpiece and determining a defect portion of the light scattered from the workpiece that is associated with defects of the workpiece;
control circuitry for activating and deactivating light selection elements of the programmable light selection array so that said selected portions of the light comprising the defect portion of the light scattered from the workpiece are selectively directed onto the photosensor element that translates said defect portion into a defect electrical signal;
defect analysis circuitry for receiving and analyzing the defect electrical signal from the photosensor element to characterize defects the workpiece.

29. The tool of claim 28 wherein the workpiece comprises an un-patterned surface.

30. The tool of claim 29 wherein the un-patterned surface comprises a semiconductor wafer.

31. The tool of claim 29 wherein the un-patterned surface comprises a semiconductor wafer having at least one un-patterned layer of material formed thereon.

32. The tool of claim 29 wherein the workpiece comprises a semiconductor wafer having a surface formed by epitaxial fabrication processes.

33. The tool of claim 29 wherein the workpiece comprises a semiconductor wafer formed using silicon germanium material.

34. The apparatus of claim 28 wherein the photodetector element operates as the photosensor element.

35. The apparatus of claim 34 wherein the programmable light selection array comprises a filter array comprising a plurality of filter elements; and
wherein the control circuitry selectively activates and deactivates the filter elements such that the defect portion of the light is selectively directed onto the photosensor element and such that the ordinary scattering portion of the light is substantially blocked from the photosensor element.

36. The apparatus of claim 34 wherein the programmable light selection array comprises a reflector array comprising a plurality of reflector elements; and
wherein the control circuitry selectively actuates the reflector elements so that the defect portion of the light is selectively reflected onto the photosensor element and so that ordinary scattering portion of the light scattered from the workpiece is selectively reflected away from the photosensor element such that substantially all of the ordinary scattering portion of the light is not detected by the photosensor element.

37. The apparatus of claim 28 wherein the photodetector element and the photosensor element are each comprised of different detector elements.

38. The apparatus of claim 37 wherein the photodetector element comprises a photodetector array comprising a plurality of photo-sensitive detector elements and wherein the photosensor element comprises a single discrete photosensitive detector device.

39. The apparatus of claim 38 wherein the single discrete photo-sensitive detector device that comprises the photosensor elements is selected from among the group of devices consisting of a photo-multiplier tube, a photodiode, and avalanche photodiode.

40. The apparatus of claim 38 wherein the programmable light selection array comprises a reflector array comprising a plurality of reflector elements; and
wherein the control circuitry selectively actuates the reflector elements to selectively direct the defect portion of the light scattered from the workpiece onto the photo sensor element.

41. The apparatus of claim 40 wherein the wherein the control circuitry selectively actuates the reflector elements to selectively direct the ordinary scattering pattern of the light scattered from the workpiece onto the photodetector array.

42. The apparatus of claim 28 wherein the processing circuitry, the control circuitry, and the defect analysis circuitry are incorporated into a single electronic circuit element.

* * * * *